April 8, 1975 E. R. DATELLO Plant Pat. 3,700
COLEUS PLANT
Filed Jan. 18, 1974
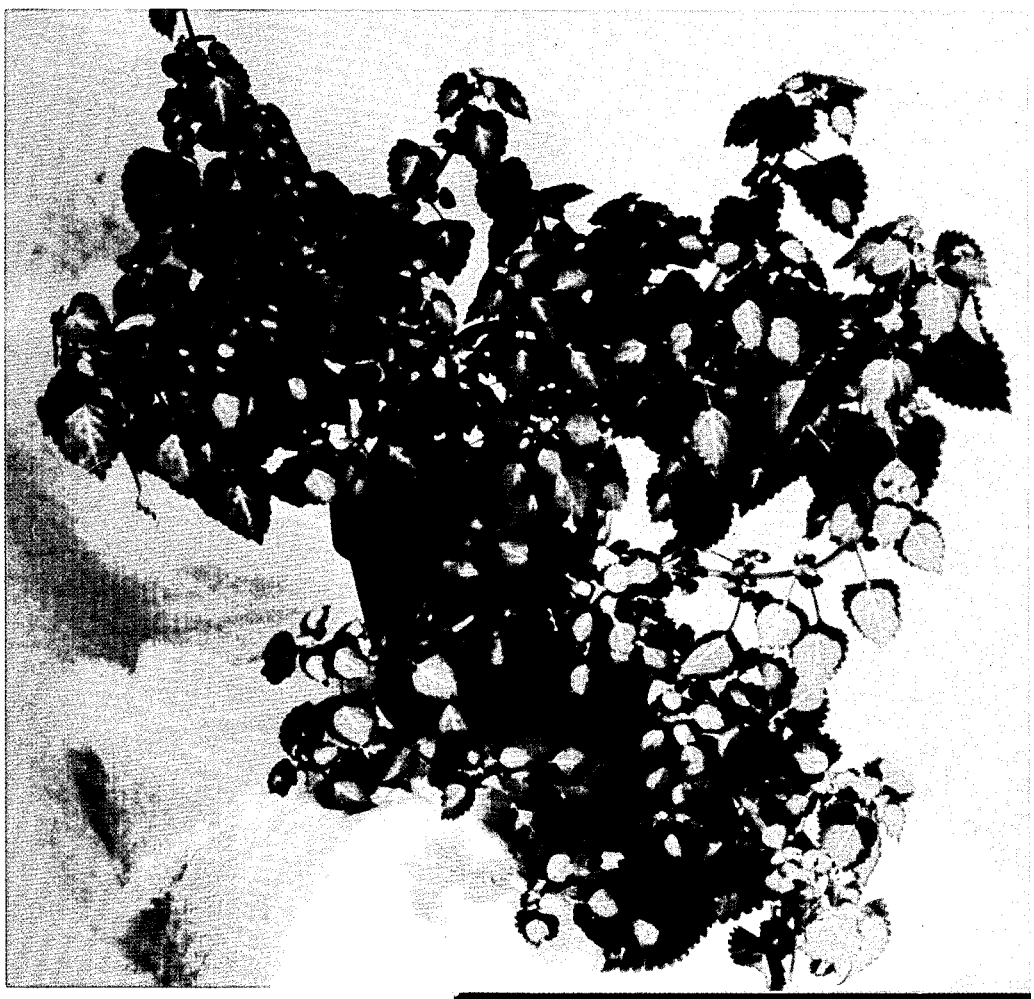
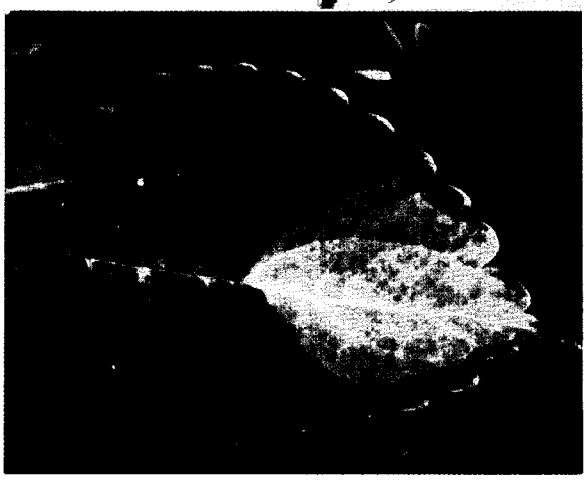

United States Patent

Plant Pat. 3,700
Patented Apr. 8, 1975

3,700
COLEUS PLANT

Enrico R. Datello, San Francisco, Calif., assignor to Datello Nurseries, Inc., Daly City, Calif.

Filed Jan. 18, 1974, Ser. No. 434,392
Int. Cl. A01h 5/12
U.S. Cl. Plt.—88 1 Claim This invention relates to a new and distinct variety of coleus plant of the trailing type.

This new variety of coleus plant was obtained as a sport discovered by applicant growing on a cultivated plant of *Coleus rehneltianus* variety "Red Trailing Queen" in applicant's greenhouse at Daly City, Calif.

The new plant resembles in growth and general appearance its parent, variety "Red Trailing Queen," differing therefrom by uniquely having a majority of the leaves bearing a single, relatively extensive, circular to heart-shaped spot of a medium yellow-green coloration thereon. The yellow-green spot extends generally outwardly from the midrib of the leaf, and generally upwardly from the apex of the leaf toward the base of the leaf, without covering the entire blade area of the leaf. The effect is suggestive of a smaller green leaf overlying a generally maroon leaf, with the smaller leaf located toward the apex of the larger one.

FIG. 1 is a photograph of the complete new plant, and FIG. 2 is a detail view of a leaf of the new plant, approximately twice life-size. As may be seen from FIG. 1, the yellow-green spot stands out in sharp contrast to the dark maroon color of the rest of the leaf. As in the parent plant, the leaf of the new plant is edged with green, but the edging is generally narrower in width than that of the parent plant, being approximately half as wide; see FIG. 2. The new plant also differs from "Red Trailing Queen" in having a slightly greater degree of maroon coloration on the leaf petioles and the stems of the plant.

This new variety of coleus plant has been found to retain its distinctive characteristics through several successive generations of asexual propagation by softwood cuttings at applicant's greenhouse in Daly City, Calif.

The following is a detailed description of my new variety of coleus plant. As to macroscopic botanic characteristics omitted from the description, the new plant may be taken to be essentially similar to the parent plant, which is a widely distributed clone. The color designations are those employed in the R.H.S. Colour Chart, 1966 Edition, issued by the Royal Horticultural Society of Great Britain.

PLANT

Form of plant: Bushy

Growth habit: Vigorous, to approximately 2½ feet in height.

FOLIAGE

Coloration:

*Upper side of laminae.*—Outside the spot: Greyed Purple Group 187A, shading rather abruptly to Greyed Purple Group 187D at the veins. Spot area: Yellow Green Group 146B, shading rather abruptly to colorless at the veins. Edging of the leaf: Green Group 137C (approximately).

*Under side of lamina.*—Coloration generally as upper side, overlain by a greenish cast, resulting in a slight apparent desaturation of the maroon color, and an apparent change in the color of the spot area to Green Group 138C, approximately.

*Spot location.*—In the majority of leaves, the spot is nearer to the apex than the base, and is generally symmetrical about the midrib.

*Spot size.*—Generally from less than a quarter of the area of the leaf to more than three-quarters of the area of the leaf, but not obscuring the maroon area entirely. In the occasional leaf, the spot extends the maximum width of the leaf without extending the full length of the leaf. A small number of leaves on the plant may be unspotted.

*Spot shape.*—Irregular, but generally circular to ovate to heart-shaped, roughly approximating the overall shape of the leaf.

*Leaf substance.*—Fleshy.

*Leaf surface texture.*—Upper surface: Scattered bristly trichomes visible to the naked eye; minutely bullulate between trichomes (30×). Trichomes in spot area colorless; magenta to maroon in maroon area of leaf. Under side: Scattered bristly trichomes along veins, colored generally as on the upper surface; glabrous to the naked eye between veins but minutely bullulate (30×); scattered minute darker spots (appearing punctuate) in area of green spot (30×).

*Leaf size (mature).*—Width: Approximately 1 to 1½ inch generally; up to 2¼ inches in some leaves. Length: Approximately 1¼ to 2 inches generally, up to 2¾ inches in some leaves.

*Leaf shape.*—Generally ovate to cordate; apex acute to acuminate; base generally truncate.

*Margin of leaf.*—Crenate, with lobes approximately 3/32 to ⅛ inch wide, approximately 1/16 to ⅛ inch deep, edging of green color (Green Group 137C) in crescent shape, extending less than full depth of lobe at center of lobe.

*Petiole.*—⅜ to 1¾ inches in length, maroon color; two distinct sizes of trichomes, the larger ones scattered, size approximately the same as the scattered trichomes of the upper leaf surface, the smaller ones densely set giving a pubescent effect, maroon in color.

*Stems of plant.*—Spotting and streaking of maroon overlying the light green stems, the spots and streaks more densely set than in the parent plant, "Red Trailing Queen," giving a substantially darker appearance to the stems of the new plant in comparison to the parent plant.

I claim:

1. A new and distinct variety of coleus plant of the trailing type substantially as described and illustrated herein, characterized primarily as to novelty by having a majority of the leaves bearing a single, relatively extensive, circular to heart-shaped spot of a medium yellow green coloration displayed on a dark maroon background.

References Cited

Exotica 3, Graf, 1963, Roehrs Co., Rutherford, N.J., pp. 5, 1013–17, 1581–2 cited of interest, AU 337.

ROBERT E. BAGWILL, Primary Examiner